US010016567B2

(12) United States Patent
Denyer et al.

(10) Patent No.: US 10,016,567 B2
(45) Date of Patent: Jul. 10, 2018

(54) COLOR IDENTIFICATION FOR DRUG DELIVERY SYSTEM

(75) Inventors: Jonathan Stanley Harold Denyer, Chichester (GB); Dirk Ernest Von Hollen, Clark, NJ (US); Anthony Dyche, Hayling Island (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 697 days.

(21) Appl. No.: 13/514,345

(22) PCT Filed: Nov. 9, 2010

(86) PCT No.: PCT/IB2010/055095
§ 371 (c)(1),
(2), (4) Date: Jun. 7, 2012

(87) PCT Pub. No.: WO2011/073806
PCT Pub. Date: Jun. 23, 2011

(65) Prior Publication Data
US 2012/0240923 A1     Sep. 27, 2012

Related U.S. Application Data

(60) Provisional application No. 61/286,993, filed on Dec. 16, 2009.

(51) Int. Cl.
*A61M 15/00*     (2006.01)

(52) U.S. Cl.
CPC .......... *A61M 15/00* (2013.01); *A61M 15/009* (2013.01); *A61M 15/0086* (2013.01); *A61M 2205/276* (2013.01); *A61M 2205/3553* (2013.01); *A61M 2205/6054* (2013.01); *A61M 2205/6081* (2013.01)

(58) Field of Classification Search
CPC ............ A61M 15/009; A61M 15/0075; A61M 15/0073; A61M 15/0086; A61M 15/0016; A61M 15/00; G06M 1/041; G06M 1/24; A61J 7/0418; A61J 7/0427
USPC ............ 128/200.11–200.24, 203.12, 203.15; 356/416, 419, 420, 421
See application file for complete search history.

(56) References Cited

U.S. PATENT DOCUMENTS

| 5,203,323 A | * | 4/1993 | Tritle ............... A61M 15/0086 128/200.23 |
| 5,810,001 A | * | 9/1998 | Genga et al. ............ 128/202.27 |
| 6,119,684 A |   | 9/2000 | Nohl et al. |

(Continued)

FOREIGN PATENT DOCUMENTS

| GB | 2263068 | * | 7/1993 |
| GB | 2263068 A |   | 7/1993 |

(Continued)

*Primary Examiner* — Todd J Scherbel
*Assistant Examiner* — Elliot S Ruddie
(74) *Attorney, Agent, or Firm* — Michael W. Haas

(57) ABSTRACT

A monitoring device includes a housing that is constructed and arranged to be removably attached to a drug delivery device for an inhaled drug. A color detector is operatively associated with the housing and constructed and arranged to detect an identifying color of at least a portion of the drug delivery device when the housing is attached to the drug delivery device and to output color information for use by a processor to, based on the detected color, identify information about the inhaled drug.

20 Claims, 4 Drawing Sheets

(56) References Cited

U.S. PATENT DOCUMENTS

| | | |
|---|---|---|
| 9,352,107 B2 | 5/2016 | Von Hollen |
| 2003/0183226 A1* | 10/2003 | Brand et al. ............. 128/200.23 |
| 2005/0005929 A1* | 1/2005 | Snyder .............. A61M 15/0086 |
| | | 128/200.23 |
| 2005/0072421 A1* | 4/2005 | Suman .................. A61M 15/00 |
| | | 128/200.23 |
| 2007/0181119 A1 | 8/2007 | Weinstein et al. |
| 2008/0164275 A1* | 7/2008 | Poutiatine et al. ............. 221/15 |
| 2009/0007905 A1* | 1/2009 | Vito .................. A61M 15/0086 |
| | | 128/200.23 |
| 2012/0026687 A1 | 10/2012 | Denyer et al. |
| 2013/0008436 A1 | 1/2013 | Von Hollen et al. |

FOREIGN PATENT DOCUMENTS

| | | |
|---|---|---|
| WO | 199312823 | 7/1993 |
| WO | 199851360 | 11/1998 |
| WO | 2006114725 A1 | 11/2006 |
| WO | 2006129301 A2 | 12/2006 |
| WO | WO2006/129301 * | 12/2006 |
| WO | WO2011058477 A1 | 5/2011 |

\* cited by examiner

Serevent Accuhaler  Flixotide Accuhaler  Seretide Accuhaler

COLOR IDENTIFICATION FOR DRUG DELIVERY SYSTEM

The invention relates generally to drug delivery devices and more particularly to a system for identifying a medication based on measured color of the devices.

It is known to deliver medications to patients for treatment of medical conditions using an aerosol medication delivery system. For example, in response to acute asthma episodes, a patient may use such a delivery system to deliver a bronchodilator such as albuterol. Typically, such a system would include a metered dose inhaler (MDI), which may be used with or without a spacer. The MDI itself is an L-shaped device that includes a pressurized medicine container and a canister holder that generally includes a mouthpiece. To operate the MDI, a user presses down on the container, causing the medicine to be expelled through the mouthpiece for inhalation by the patient. For systems that include a spacer, the spacer provides additional air volume to allow better mixing of the aerosolized medicine with ambient air prior to inhalation.

A similar device is the dry powder inhaler (DPI). In a DPI, a measured dose of powdered medication may be delivered without any propellant, the user's inspiratory flow providing the air volume for pulling the powdered medication into the user's lungs. In a typical device of this type, actuating the DPI loads a measured volume of powdered medication into a dosing chamber. The user then inhales, drawing air and the medication into his or her lungs. For children in particular, DPI devices may be easier to use as, unlike MDI devices, there is no need to coordinate actuation with inspiration.

Nebulizers may also be used for delivery of medications to a patient's lungs. A nebulizer includes an air source and a fluid medicine reservoir. The air source is used to provide a strong flow of air through the fluid, aerosolizing it for delivery to the patient. In general, nebulizers are bulky and inconvenient compared to MDI and DPI devices.

It may be useful for an administering medical team to monitor the use of inhaled medications for compliance with the prescribed regimen.

A monitoring device includes a housing that is constructed and arranged to be removably attached to a drug delivery device for an inhaled drug. A color detector is operatively associated with the housing and constructed and arranged to detect an identifying color of at least a portion of the drug delivery device when the housing is attached to the drug delivery device and to output color information for use by a processor to, based on the detected color, identify information about the inhaled drug.

Another aspect of an embodiment of the present invention includes a broadband light source for illuminating the drug delivery device and a color-sensitive detector to detect the identifying color.

Another aspect of an embodiment of the present invention includes multiple, relatively narrow-band light sources for sequentially illuminating the drug delivery device, a color-insensitive detector, and analyzing functionality to combine detected information to determine the identifying color.

As will be appreciated by those of skill in the art, a color detecting device in accordance with an embodiment of the invention may find application in medicine delivery systems other than inhaled drug delivery systems. In this regard, such devices may include sensors similar to those described herein with respect to inhaled drug delivery systems for detecting color information relating to identification of a drug type or dose. Such sensors may be used, for example, in collecting, storing and/or reporting compliance by a patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 5:
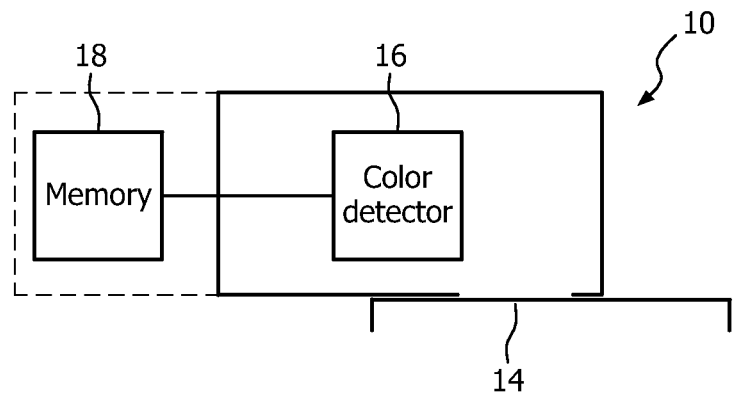
Figure 6:
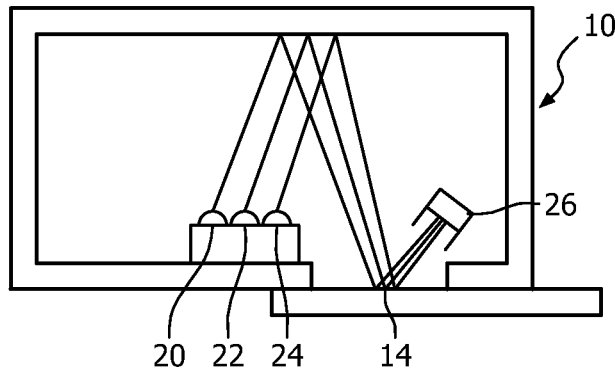
Figure 7:
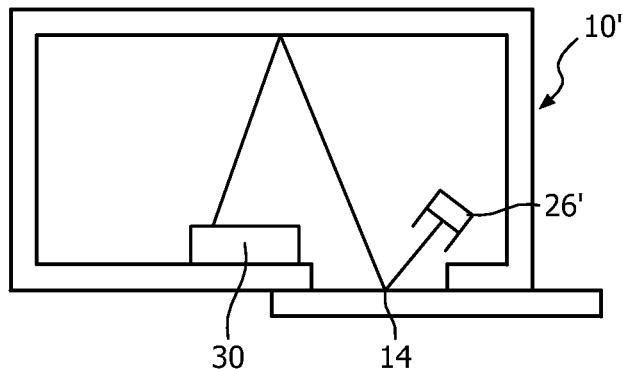

FIG. 5 schematically illustrates a sensor for use in a monitor in accordance with an embodiment of the invention;

FIG. 6 schematically illustrates a scanning color sensor for use in a monitor in accordance with an embodiment of the invention; and FIG. 7 schematically illustrates a white light sensor for use in a monitor in accordance with an embodiment of the invention.

As described above, drug delivery systems for inhaled medicines include, but are not limited to, MDI, DPI and nebulizers. In general, manufacturers of such delivery systems use color information to inform a user regarding the nature of the medication. Color information may be relevant, for example, to type, amount, and/or strength of medication. In both the United States and the European Union, pharmaceutical packaging is regulated, and a manufacturer may not, in general, make changes to the packaging, including the plastic material, without licensing approval. As a result, color information should be a relatively stable identification method for most drug delivery systems.

In this regard, the regulator ensures that colors are approved and controlled to ensure that there is the minimum risk of confusion on the part of the public or medical professionals. For each manufacturer colors will generally be different for each type of drug, though drugs of the same type from different manufactures may have similar but not identical colors, e.g., bronchodilators may be supplied in blue delivery systems, while steroids may be supplied in brown delivery systems.

Figure 1:
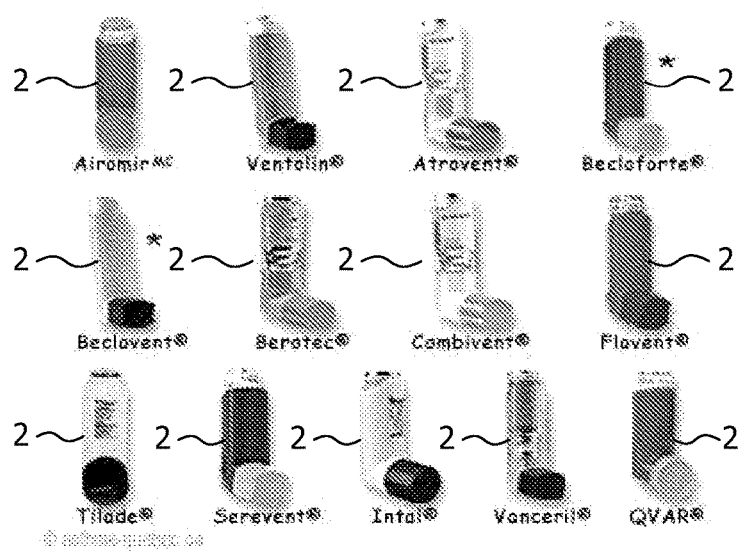
FIG. 1 illustrates a number of different MDIs, each having differing coloration for use with a device in accordance with an embodiment of the invention.

FIG. 1 shows 13 different MDIs 2, each MDI 2 containing a different medicine. As may be seen, each is of a different color, though the colors are rendered in grey scale for the purposes of this application. By way of example only, in the original, full-color figure, the three along the right hand side are different shades of red and orange, while the upper left hand corner MDI is blue and the lower left hand corner is yellow. Others in the FIG. each have their own distinctive coloration.

Figure 2:
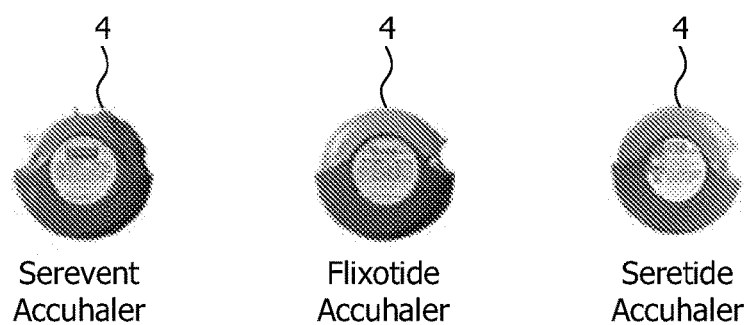
FIG. 2 illustrates a number of different DPIs, each having differing coloration for use with a device in accordance with an embodiment of the invention.

Likewise, FIG. 2 illustrates three different DPIs 4, each a different color. By way of example, the three DPIs are green, red and purple, from left to right. In nebulizers, such as I-neb® from Philips Respironics, color of a portion of the metering chamber and/or a removable control disc can inform a user regarding the amount of medication that will be provided with each application.

Figure 3:
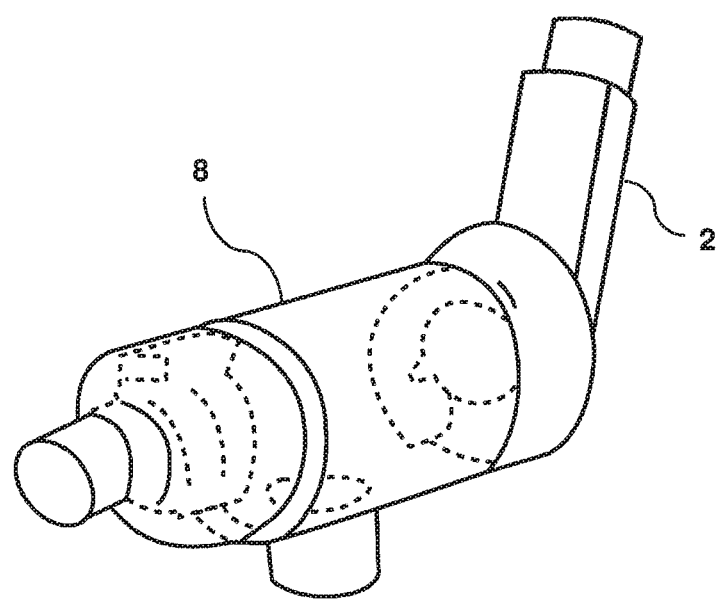
FIG. 3 illustrates an MDI along with a spacer for use with a device in accordance with an embodiment of the invention.
Figure 4:
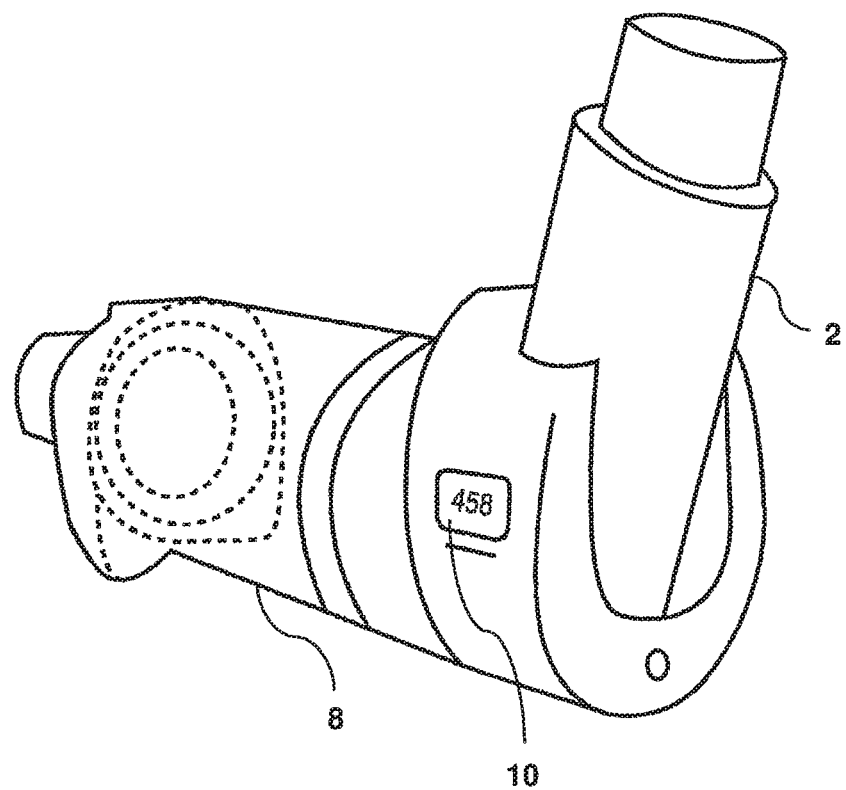
FIG. 4 illustrates an MDI and spacer, including a monitor in accordance with an embodiment of the invention.

FIG. 3 illustrates an MDI 2 inserted into a spacer 8. FIG. 4 illustrates a similar MDI 2 inserted into a spacer 8 that incorporates a monitor 10 in accordance with an embodiment of the invention.

A monitor 10 in accordance with an embodiment of the invention is a non-contact device that does not generally engage directly with any drug product, thereby reducing likelihood of contamination when the drug canister is changed, nor does it generally require cleaning to remove drug residue. In this regard, a non-contact color recognition system may be permanently or removably mounted to the drug delivery device.

FIG. 5 illustrates an embodiment in which the monitor 10 includes an opening 12 such that a portion 14 of the drug delivery device is exposed to the monitor when the device is inserted. A color detecting device 16 captures color information from the portion 14, and may provide the color information to a memory 18, which may be internal to the monitor 10, or may be associated with a separate device.

In an embodiment illustrated in FIG. 6, the monitor includes three LEDs, 20, 22, 24, which may be, for example, red, blue and green respectively. In this approach, the LEDs 20, 22, 24 are controlled by a controller and powered with a power source, not shown. A light detector 26, such as a photodiode, is positioned to receive light reflected from the portion 14 of the drug delivery device, when illuminated by the LEDs. It is useful to ensure that the detector 26 does not receive light directly from the LEDs but rather is shielded so that it receives light primarily from the target portion 14. The controller sequentially activates the LEDs, thereby performing a color sequential scan. The received light at the detector 26 for each color signal may then be combined to produce color information indicative of drug information.

As will be appreciated, similar methods may be used based on different LED colors, and the scope of the present invention should not be considered to be limited to an RGB system. Likewise, though illustrated as first reflecting from a remote surface of the monitor, the LED light need not do so, and may directly impinge on the portion 14 of the surface of the drug delivery device.

In an alternate approach, illustrated in FIG. 7, the LEDs of the monitor 10' may be replaced with a white light source 30 and the detector 26 may be replaced with a color detector 26', such as a CCD. For example, the color detector 26' may be a CCD using a color filter array such as a Bayer filter, though other color filter arrays may find application within the scope of the present invention.

In this arrangement the color detector receives light from the white light source reflected from the inhaler body, the controller then analyzes the signal generated by the detector to determine the color of the inhaler. When the controller has determined the color of the inhaler it can be recorded in the device memory 18 as part of the treatment compliance record.

The color recorded in the treatment compliance record can then be compared with a master list of inhaler colors and the type of inhaler identified to the clinician or patient. This identification may be completed in the device or remotely in a PC, when the data is downloaded or as part of an internet based system incorporating a server. Alternately, a function-specific reader could be employed. The download functionality may be via a plug-in connector such as USB or other bus, or may be wireless, for example with an RFID-type reader or other radio device.

In an embodiment, the monitor 10 may further include a sensor to determine when a dose is administered. Such a sensor may be based on a number of different sensing approaches. In an embodiment, a circuit may be completed each time the inhaler is actuated, incrementing a use count to be stored in the memory 18. While the specifics of such a detector are not critical to the present application, one of skill in the art would appreciate that a variety of approaches are available. For example, airflow through a portion of the delivery device could be detected, sound or pressure sensors could be used, or optical detectors could be used.

In embodiments, the monitor 10 may include functionality for discriminating based on the detected color, and outputting identifying information for the monitored drug delivery system. This may include, for example, stored color values associated with particular drug delivery devices and processing capability for comparing detected color with the stored color values. Likewise, the monitor 10 may include alarm functionality wherein when the detected color does not match a preselected color associated with a patient's prescribed medication, the alarm is sounded to warn the patient not to use the medication.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A drug delivery system comprising:
a spacer having an interior volume, and arranged to be removably coupled to a drug delivery device for an inhaled drug, the drug delivery device including a colored medicine container and a mouthpiece, the spacer having an aperture configured to receive the drug delivery device, including the colored medicine container thereof, at a first end thereof, the spacer including a monitoring device comprising:
an opening that exposes a portion of the colored medicine container to the monitoring device; and
a color detector disposed proximate to the opening and configured to differentiate between multiple identifying colors including at least a first identifying color, a second identifying color, and a third identifying color, the color detector constructed and arranged to:
detect an identifying color from the multiple identifying colors of the portion of the colored medicine container inserted within the interior volume of the spacer, when the spacer is coupled to the drug delivery device; and output color information for use by a processor to, based on the detected identifying color of the colored medicine container, identify information about the inhaled drug, wherein identifying information about the inhaled drug includes comparing the identified color of the colored medicine container to a plurality of colors, each color associated with a particular inhaled drug, the color detector comprising a plurality of light sources that produce different colored light and a photodetector, the light sources and the photodetector configured such that, when the spacer is coupled to the drug delivery device, light from the light sources is directed so that it reflects from an inner surface of the monitoring device and the portion of the colored medicine container before impinging on the photodetector.

2. The drug delivery system as in claim 1 further comprising:
a detector, operatively associated with the spacer and constructed and arranged to detect actuation of the drug delivery device and to output a detection signal to the processor in response.

3. The drug delivery system as in claim 1, wherein the color detector further comprises:
a controller configured and arranged to controllably operate the light sources in sequence; and
an analyzer, configured and arranged to combine sequentially detected signals from the photodetector and to mix them to produce the color information.

4. The drug delivery system as in claim 1, wherein the color detector further comprises:
a broadband light source; and
the photodetector.

5. The drug delivery system as in claim 4, wherein the photodetector comprises a CCD.

6. The drug delivery as in claim 5, wherein the CCD comprises a color filter array.

7. The drug delivery system as in claim 1, further comprising, a memory, in communication with the color detector, the memory having stored therein a plurality of stored color information data, each stored color information datum associated with a particular inhaled drug, and wherein the processor is configured and arranged to compare the detected color with the stored color information data to identify information about the inhaled drug.

8. The drug delivery system as in claim 1, further comprising an alarm, wherein when the identified information about the inhaled drug does not correspond to a preselected inhaled drug prescribed to a user, the alarm produces an audible or visible indicator.

9. The drug delivery system as in claim 1, wherein the drug delivery device further comprises a holding portion coupled to the mouthpiece of the drug delivery device, wherein the holding portion encloses at least a portion of the colored medicine container, and wherein the spacer encloses the mouthpiece of the drug delivery device and at least a portion of the holding portion.

10. The drug delivery system as in claim 1, wherein the spacer has a tubular shape.

11. A method of monitoring use of a drug delivery device, the drug delivery device including a colored medicine container and a mouthpiece, the method comprising:
removably coupling a spacer having an interior volume to the drug delivery device, the spacer having an aperture configured to receive the drug delivery device, including the colored medicine container thereof, at a first end thereof, the spacer including a monitoring device comprising an opening that exposes a portion of the colored medicine container to the monitoring device;
detecting color information of the colored medicine container inserted within the interior volume of the spacer using a color detector, the color detector disposed proximate to the opening, the color detector configured to differentiate between multiple identifying colors including at least a first identifying color, a second identifying color, and a third identifying color;
the detecting of the color information comprising producing different color light with a plurality of light sources and detecting reflected light with a photodetector, wherein the monitioring device houses the light sources and the photodetector, the light sources and the photodetector configured such that, when the spacer is coupled to the drug delivery device, light from the light sources is directed so that it reflects from an inner surface of the monitoring device and the portion of the colored medicine container before impinging on the photodetector;
determining from the detected color information, drug information relating to a type, dosage amount and/or strength of a drug contained in the drug delivery device, wherein determining drug information includes comparing the detected color information of the colored medicine container to a plurality of colors, each color associated with a particular drug; and
storing the drug information.

12. The method as in claim 11, further comprising:
after the storing, transmitting the drug information to a storage location remote from the drug delivery device.

13. The method as in claim 12, wherein the storage location remote from the drug delivery device is Internet accessible.

14. The method as in claim 11, wherein the detecting the color of the colored medicine container further comprises:
sequentially illuminating the portion of the colored medicine container with the different colored light; and
analyzing detected sequentially reflected light from the colored medicine container to produce the color information.

15. The method as in claim 11, wherein the detecting the color of the colored medicine container further comprises:
illuminating the portion of the colored medicine container with broadband illumination; and
detecting the color information with the photodetector.

16. The method as in claim 15, wherein the photodetector comprises a CCD.

17. The method as in claim 11, further comprising:
comparing detected color information to an expected color information corresponding to a particular drug, and when the detected color information does not match the expected color information, indicating a mismatch to a user.

18. The drug delivery system as in claim 1, wherein the spacer further comprises another mouthpiece attached at a second the spacer, and wherein the spacer provides fluid communication between the mouthpiece of the drug delivery device and the another mouthpiece.

19. The method as in claim 11, wherein the spacer further comprises another mouthpiece attached at a second end of the spacer, and wherein the spacer provides fluid communication between the mouthpiece of the drug delivery device and the another mouthpiece.

20. The method as in claim 11, wherein the drug delivery device further comprises a holding portion coupled to the mouthpiece of the drug delivery device, wherein the holding portion encloses at least a portion of the colored medicine container, and wherein the spacer encloses the mouthpiece of the drug delivery device and at least a portion of the holding portion.

* * * * *